(12) United States Patent
Grosso et al.

(10) Patent No.: US 11,510,775 B2
(45) Date of Patent: Nov. 29, 2022

(54) CORNEAL IMPLANT

(71) Applicants: Edoardo Grosso, Moncalieri (IT); Emiliano Lepore, Martignacco (IT)

(72) Inventors: Edoardo Grosso, Moncalieri (IT); Emiliano Lepore, Martignacco (IT)

( * ) Notice: Subject to any disclaimer, the term of this patent is extended or adjusted under 35 U.S.C. 154(b) by 0 days.

(21) Appl. No.: 16/972,924

(22) PCT Filed: May 31, 2019

(86) PCT No.: PCT/IB2019/054540
§ 371 (c)(1),
(2) Date: Dec. 7, 2020

(87) PCT Pub. No.: WO2019/234571
PCT Pub. Date: Dec. 12, 2019

(65) Prior Publication Data
US 2021/0244529 A1  Aug. 12, 2021

(30) Foreign Application Priority Data
Jun. 8, 2018  (IT) .......................... 102018000006146

(51) Int. Cl.
*A61F 2/14*  (2006.01)

(52) U.S. Cl.
CPC .............. *A61F 2/147* (2013.01); *A61F 2/142* (2013.01); *A61F 2/15* (2015.04)

(58) Field of Classification Search
CPC ........................ A61F 2/142; A61F 2/15; A61F 2002/1681–16903; A61F 2/1451; A61F 2/147

See application file for complete search history.

(56) References Cited

U.S. PATENT DOCUMENTS 8,409,177 B1 * 4/2013 Lai .......................... A61F 9/008
 606/4
9,204,961 B2 * 12/2015 Cuevas ..................... A61F 2/16
(Continued)

FOREIGN PATENT DOCUMENTS

SU    1160623 A  * 10/1987  ............... A61F 2/14
WO   97/28759        8/1997
(Continued)

OTHER PUBLICATIONS

International Search Report for PCT/IB2019/054540 dated Aug. 14, 2019, 4 pages.
(Continued)

*Primary Examiner* — Javier G Blanco
(74) *Attorney, Agent, or Firm* — Nixon & Vanderhye P.C.

(57) ABSTRACT

Corneal implant (1) designed for correcting irregularities of the corneal curvature of a subject, the implant (1) having a generally dome-shaped structural body (2) configured to impose a regular curvature to the corneal portions designed to be in contact with the implant, wherein the structural body comprises an outer peripheral ring (10) and an inner reticular structure (20), wherein the inner reticular structure (20) comprises at least one first and one second series of beams (21, 22) intersecting each other, the beams (21) of the first series having a respective first end (31) connected to the outer peripheral ring (10), wherein the total area of void portions (24) within the meshes of the reticular structure (20) is between 50 and 99.9% of the surface area of the reticular structure (20).

3 Claims, 3 Drawing Sheets

(56) References Cited

U.S. PATENT DOCUMENTS

| | | | | |
|---|---|---|---|---|
| 2004/0243231 A1* | 12/2004 | Koziol | ............... | A61F 2/147 |
| | | | | 623/5.12 |
| 2006/0235513 A1* | 10/2006 | Price | ............... | A61F 2/147 |
| | | | | 623/5.14 |
| 2006/0271185 A1* | 11/2006 | Silvestrini | ............... | G02C 7/165 |
| | | | | 623/5.16 |
| 2007/0168025 A1* | 7/2007 | Darougar | ............... | A61F 2/142 |
| | | | | 623/5.14 |
| 2009/0204207 A1* | 8/2009 | Blum | ............... | G02C 7/083 |
| | | | | 623/4.1 |
| 2010/0069915 A1 | 3/2010 | Shiuey | | |
| 2014/0074232 A1* | 3/2014 | Soares | ............... | A61F 2/147 |
| | | | | 623/5.12 |
| 2015/0342725 A1* | 12/2015 | Cuevas | ............... | A61F 2/16 |
| | | | | 623/6.16 |

FOREIGN PATENT DOCUMENTS

| | | | | |
|---|---|---|---|---|
| WO | WO-2006009490 A1 * | 1/2006 | ............ | A61F 2/142 |
| WO | 2006/113634 | 10/2006 | | |

OTHER PUBLICATIONS

Written Opinion of the ISA for PCT/IB2019/054540 dated Aug. 14, 2019, 7 pages.

* cited by examiner

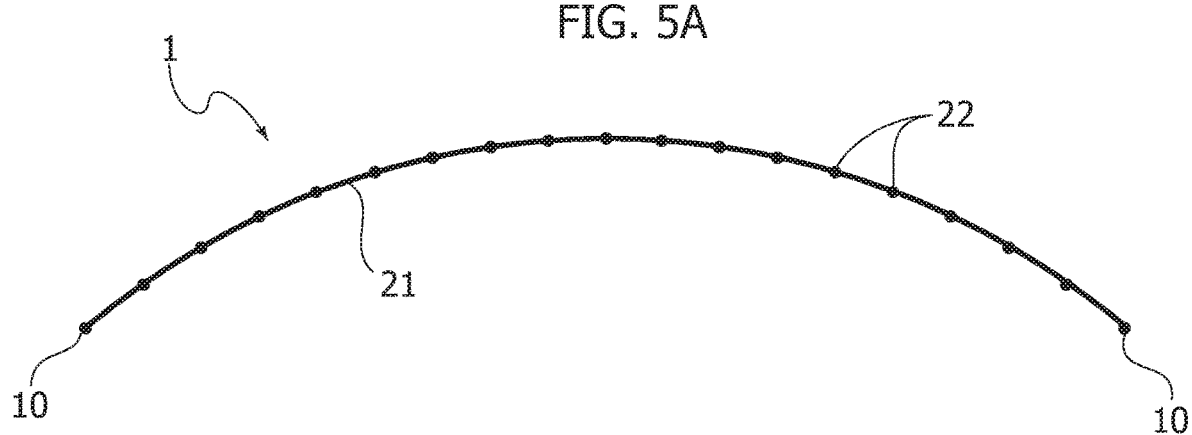
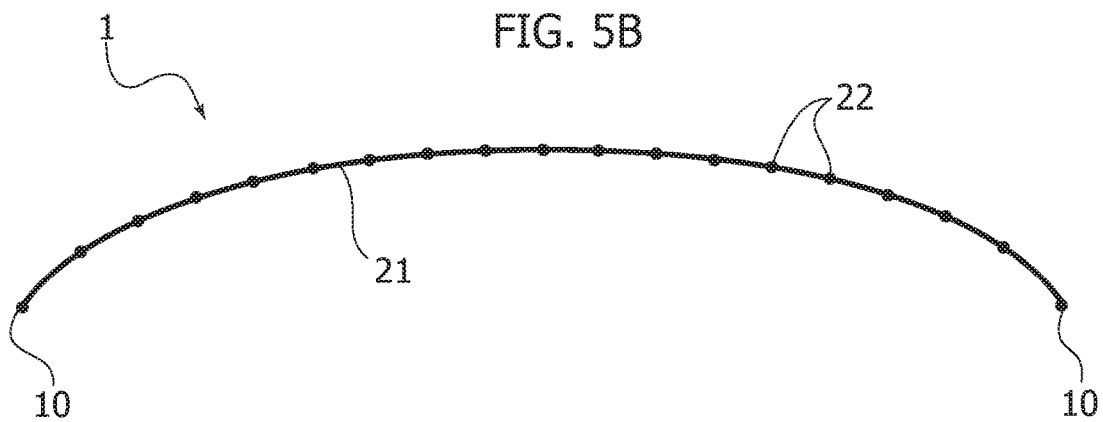

CORNEAL IMPLANT

This application is the U.S. national phase of International Application No. PCT/IB2019/054540 filed May 31, 2019 which designated the U.S. and claims priority to IT Patent Application No. 102018000006146 filed Jun. 8, 2018, the entire contents of each of which are hereby incorporated by reference.

FIELD OF THE INVENTION

The present description relates to a corneal implant intended to correct irregularities in the curvature of a subject's cornea.

BACKGROUND OF THE INVENTION

A corneal implant is an implantable device intended to impose a substantially regular curvature to the cornea, so as to restore an optimal optical situation intended to reduce or eliminate optical aberrations that compromise, for example, visual acuity or contrast sensitivity.

Treatments known and used—to date—for treating corneal aberrations induced by curvature irregularities are the following:

1. Contact Lenses (LC): lenses placed in direct contact with the external surface of the cornea, made of materials of different rigidity and oxygen permeability. Contact lenses are easily applicable, they allow accurate correction of the global ocular refractive error, but have some disadvantages such as the risk of contracting infection by the subjects who wear them, intolerance in the case of advanced keratoconus or the development of immune reactions at the conjunctival level because of contact with the surface of the lens.

2. ICRS (Intra corneal ring segments): segments of circular rings in polymeric material, mainly PMMA, of variable diameter and thickness. These devices, inserted into the thickness of the corneal stroma, are intended for treating mild myopias (following flattening of the optic area of the cornea) or keratoconus. ICRS guarantee the reversibility of the implant (being easily removable) and the preservation of a free optical zone. However, ICRS have a limited capacity to impose a regular curvature to the cornea, a relatively high risk of extrusion, the persistence of irregularities of the anterior or posterior surfaces of the cornea due to the high thickness of the device in relation to the corneal thickness, as well as induction of stromal fibrosis.

3. Ablative treatment with excimer laser: technology applied in the refractive field for 25 years, usable both as a surface treatment (PRK) and as a stromal treatment (LASIK). The regularization of the cornea with this technique occurs by subtraction of tissue. The main advantage of this intervention is the absence of foreign bodies implanted at the corneal level. Ablative treatment, however, is only capable of remodeling the anterior surface of the cornea by removing tissue, without the possibility of modifying the shape of the posterior corneal surface which, if irregular, can induce considerable optical aberrations (such as in the case of keratoconus). Moreover, this treatment can cause corneal ectasia in the event of insufficient residual corneal thickness and does not guarantee an adequate correction when the corneal thickness is limited.

4. Treatment with incisional refractive surgery techniques (radial keratotomies and arcuate keratotomies): execution of partial thickness corneal incisions with the object of curving the areas where the incisions are made and of flattening the areas adjacent to the incisions. These techniques can be advantageous with respect to ablative treatments, since they do not reduce the corneal thickness, but are essentially characterized by a poor predictability of the refractive result and by a high risk of inducing secondary corneal ectasias.

Since the 1980s, various types of corneal implants have been developed to correct the curvature of the cornea, which can overcome the disadvantages of known techniques.

Whole ring corneal implants have been developed, as described, for example, in U.S. Pat. Nos. 5,645,582, 4,671,276, WO-A-2006/113634 and US-A-2002/0013622.

These corneal implant devices, although better than ICRS, still have the main disadvantage of a reduced ability to impose a pre-defined curvature on the cornea, as they are characterized by a reduced size in radial cross-section: this means that their main role is that of flattening the corneal portions in which they are implanted if they are highly curved. The reduced width of these ring structures prevents them from defining a precise shape for the cornea, as they exert their action on a very small surface along a radial direction.

Circular-shaped corneal implants comprising a central opening are described, for example, in US-A-2014/0074232. Other types of corneal implants consisting of an opaque circular mask provided with a free central hole or coupled with an optical lens are known, for example, WO-2011/069059, WO-A-93/12735 and US-A-2006/0271185. These implants are intended to increase the depth of focus of the human eye, a useful strategy, for example, for correcting presbyopia. The central opening acts as a pinhole by selecting the paraxial rays that pass through the ocular diopter. Moreover, these devices have a structure that follows the curvature of the ocular anatomical structure in which they are implanted.

At present, corneal implants that allow satisfactory treatment of corneal curvature irregularities are not yet available.

SUMMARY OF THE INVENTION

Taking into consideration these suppositions, improved and more effective solutions allowing the imposition of a substantially regular curvature to the cornea, with respect to known implantable corneal devices, are therefore required.

In accordance with the invention, the aforesaid object is achieved thanks to the solution specifically recalled in the attached claims, which form an integral part of the present description.

One embodiment of the present invention relates to a corneal implant intended to correct irregularities in the curvature of the cornea of a subject, in which the implant has a generally dome-shaped structural body configured to impose a regular curvature on the corneal portions intended to be in contact with the implant. The structural body comprises an outer peripheral ring and an inner reticular structure, which, in turn, comprises at least one first and one second series of beams intersecting each other so as to form a series of solid portions and a series of void portions, where the beams of the first series are connected to the outer peripheral ring through a respective first end, in which the overall area of the void portions within the meshes of the reticular structure is between 50 and 99.9% of the surface area of the reticular structure.

BRIEF DESCRIPTION OF THE DRAWINGS

The invention will now be described in detail, by way of non-limiting illustrative example, with reference to the attached figures, wherein:

FIGS. 5A and 5B are cross-sectional views of different embodiments of the corneal implant subject of the present description.

DETAILED DESCRIPTION OF THE INVENTION

Figure 1:
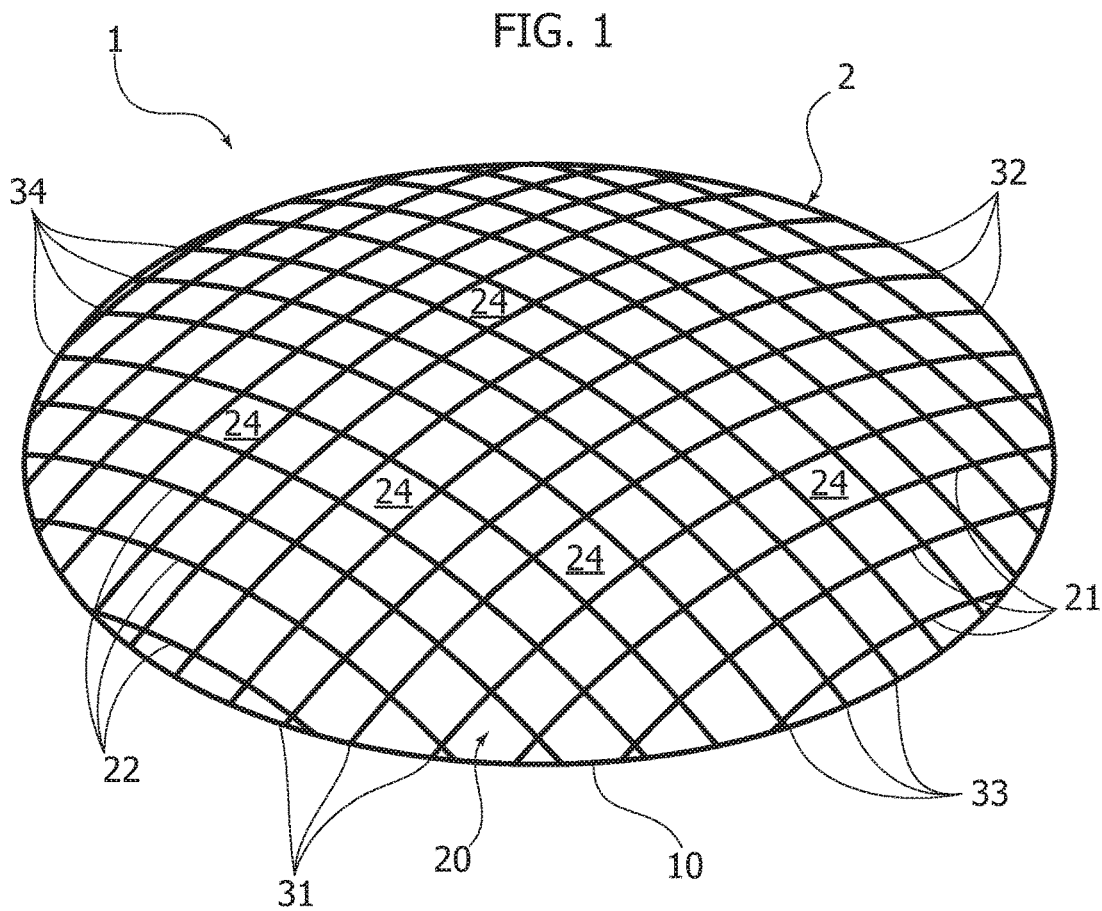
FIGS. 1 and 2 are perspective views of two different embodiments of the corneal implant subject of the present description.

The invention will now be described in detail, by way of non-limiting illustrative example.

In the following description, there are numerous specific details to provide a thorough understanding of the embodiments. The embodiments may be implemented in practice without one or more of the specific details, or with other methods, components, materials, etc. In other cases, well-known structures, materials or operations are not shown or described in detail to avoid obscuring certain aspects of the embodiments.

Throughout the present specification, the reference to "an embodiment" or "embodiment" means that a particular configuration, structure, or characteristic described in connection with the embodiment is included in at least one embodiment. Therefore, the appearance of expressions "in a certain embodiment" or "in an embodiment" in various point throughout this specification does not necessarily always refer to the same embodiment. Moreover, the particular details, structures or characteristics can be combined in any suitable way in one or more embodiments.

The headings used here are used merely for convenience and do not interpret the object or meaning of the embodiments.

The corneal implant subject of the present description is intended for treating patients suffering from an irregular conformation of the cornea. The corneal implant described here is, in fact, able to impose its curvature on the cornea in order to correct the pathological deformations of the cornea itself thanks to the rigidity of its structure and the presence of a continuous outer peripheral ring capable of stabilizing the three-dimensional conformation of the implant itself.

Furthermore, the use of an outer peripheral ring in the corneal implant described here, and where present, a substantially continuous, uninterrupted, innermost peripheral ring, allows the implant to slide into the corneal stroma during the implantation process, making the surgical implant method substantially atraumatic; a margin formed of free ends would constitute an irregular surface, posing a disadvantage in the implant as it would not be suitable for sliding between the corneal layers.

Moreover, the corneal implant which is the subject of the present description has been designed to have a large area of its surface substantially free or empty, in order not to interfere at all, or at least only minimally, with the entry of light into the eye.

In one embodiment of the present description, the corneal implant has a dome-shaped structural body configured to impose a regular curvature on the corneal portions intended to be in contact with the implant. The structural body comprises an outer peripheral ring and an inner reticular structure, which, in turn, comprises at least one first and one second series of beams intersecting each other, where the beams of the first series are connected to the outer peripheral ring through a respective first end, in which the overall area of the void portions within the meshes of the reticular structure is between 50 and 99.9% of the surface area of the reticular structure.

With reference to FIG. 1, the corneal implant identified with the numerical reference 1 has a generally dome-shaped structural body 2 comprising an outer peripheral ring 10 and an inner reticular structure 20.

The outer peripheral ring has a continuous surface. This characteristic allows rendering the insertion of the implant atraumatic, as highlighted above.

The inner reticular structure 20 comprises at least one first and one second series of beams 21, 22 intersecting each other, where the beams 21, 22 of both the first and second series have both ends 31, 32, 33, 34 connected to the outer peripheral ring 10.

The first and second series of intersecting beams 21, 22 extend in a radial direction with respect to the outer peripheral ring 10.

The outer peripheral ring 10 can preferably assume a circular or elliptical configuration.

As shown in FIG. 1, the structural body is devoid of inner circular openings coaxial with the outer peripheral ring. Producing an implant according to this embodiment, without central openings favors the homogeneous correction of the surface of the cornea, achieving a satisfactory therapeutic result quickly.

The dome-shaped structural body 2 may have a curvature such as to give rise in a sagittal cross-section to a substantially semi-circular or semi-elliptical profile, or a customized profile based on the needs of the patient, as illustrated in FIGS. 5A and 5B.

The overall area of the void portions 24 within the meshes of the reticular structure 20 is between 50 and 99.9%, preferably between 75 and 98%, of the total surface area of the reticular structure 20.

In another embodiment, the inner reticular structure can comprise an innermost peripheral ring. The presence of an innermost peripheral ring can lead to an increase in the stability of the structure.

Figure 2:
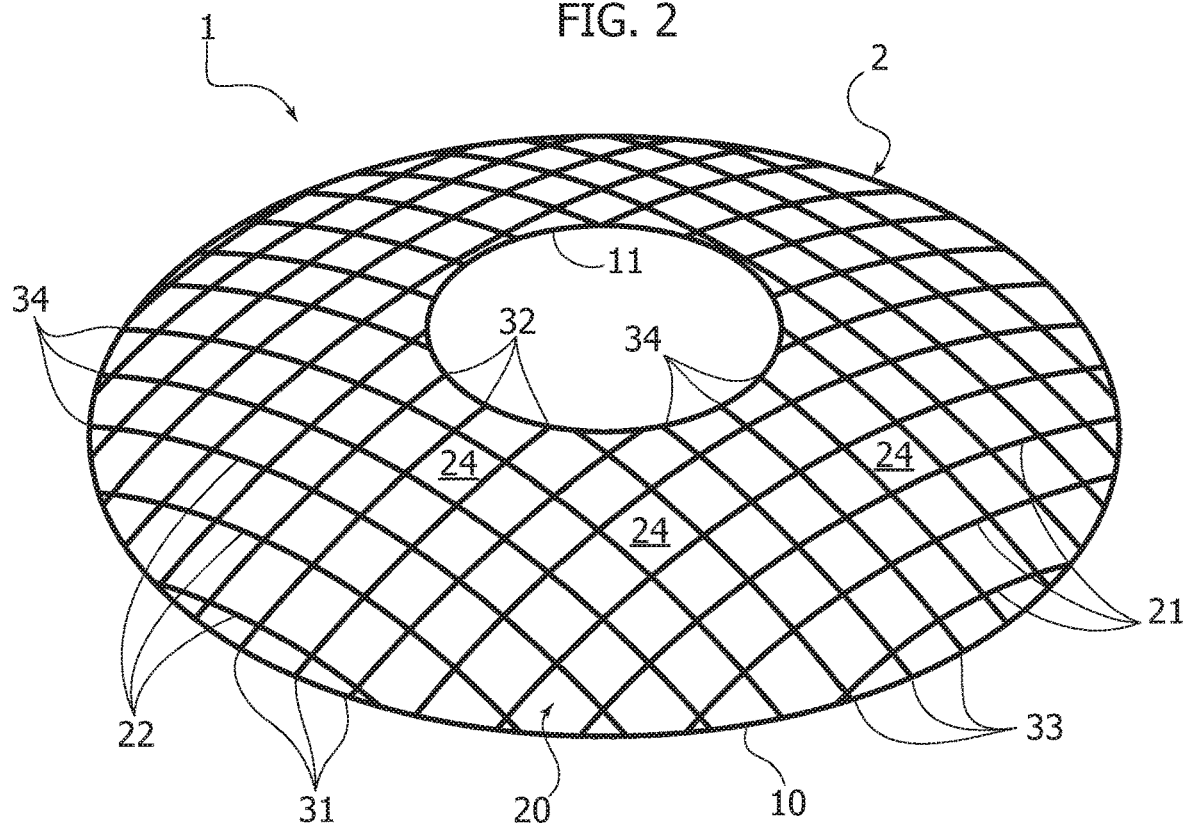

FIG. 2 shows a variant embodiment of the corneal implant 1 illustrated in FIG. 1, where the same numerical references indicate analogous elements.

The inner reticular structure 20 of the implant 1 comprises an inner peripheral ring 11, so as to create a substantially empty central zone of the corneal implant 1. This embodiment envisages that a portion of the beams 21, 22 of the first and second series, in particular the beams 21, 22 which by position would intersect the innermost peripheral ring 11, have the respective second end 32, 34 connected to the innermost peripheral ring 11, the remaining portion of the beams 21, 22 of the first and second series connected to the outer peripheral ring 10 through the respective second end 32, 34.

The outer peripheral ring 10 and the innermost peripheral ring 11 can assume a circular or elliptical configuration and are preferably coaxial. The inner reticular structure 20 consequently has a circular or elliptical ring configuration.

As shown in FIG. 2, the beams 21, 22 of the first series and of the second series extend in a radial direction with respect to the outer peripheral ring 10.

Also in the embodiment of FIG. 2 that provides a central opening, the curvature of the cornea is also regularized in the free central portion of the cornea. This result is obtained as a consequence of the regularity of shape that is imposed on the surrounding corneal annular portion by the annular reticular structure of the implant.

Moreover, the presence of an outer peripheral ring 10 and an inner peripheral ring 11 gives the implant greater conformational stability, which results in an effective treatment of corneas with particularly irregular surfaces.

Figure 3:
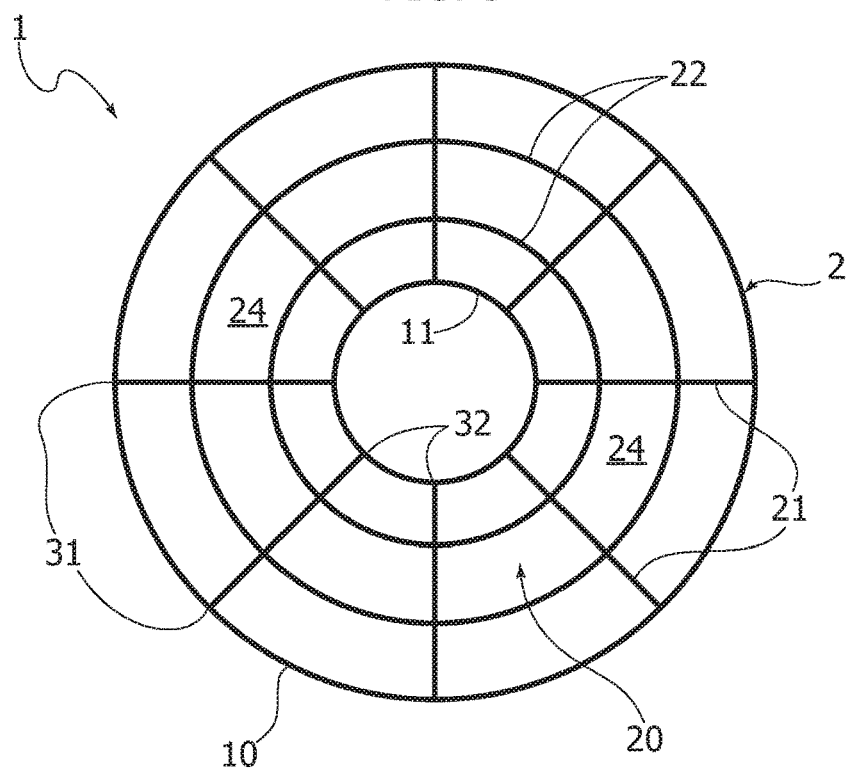
FIGS. 3 and 4 are plan views of two different embodiments of the corneal implant subject of the present description.

According to a further embodiment of the corneal implant 1 as shown in FIG. 3, the beams 22 of the second series comprise annular beams arranged substantially concentrically to each other.

The beams 21 of the first series, extending in a substantially radial direction with respect to the outer peripheral ring 10, have the respective first end 31 connected to the outer peripheral ring 10 and the respective second end 32 connected to the innermost peripheral ring 11.

Figure 4:
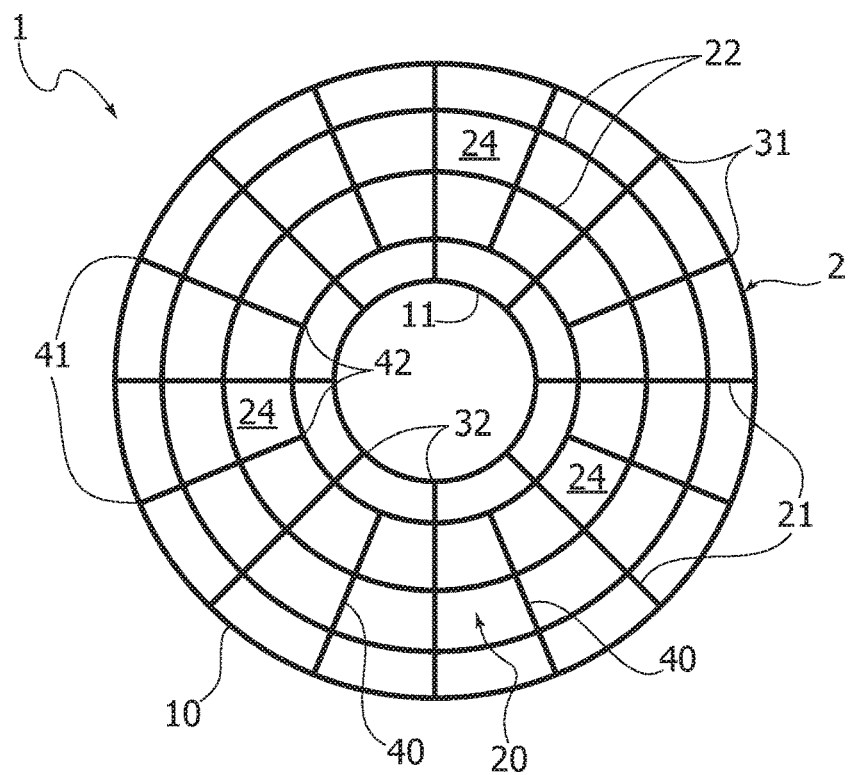

In another embodiment as shown in FIG. 4, the inner reticular structure 20 of the corneal implant 1 comprises a third series of beams 40, which have a respective first end connected to the outer peripheral ring 10 and a respective second end 42 connected to an annular beam 22 defining a circumference or perimeter greater than the circumference or perimeter defined by the innermost peripheral ring 11.

An implant according to the embodiment shown in FIG. 4 is provided with stability and flexibility, which make it suitable for effectively imparting regular corneal curvatures. In FIG. 4 in particular, this annular beam 22 is represented by the first annular beam starting from the innermost peripheral ring 11, however in varying embodiments this beam 22 can also be represented by annular beams radially more distant from the innermost peripheral ring 11.

The beams 21, 40 of the first and third series extend in a substantially radial direction with respect to the outer peripheral ring 10.

With reference to the embodiments shown in FIGS. 3 and 4, the beams 21 of the first series define, together with the outer peripheral ring 10 and the innermost peripheral ring 11, a plurality of sectors of the structural body 2 substantially having a configuration as an arc of a circular or elliptical annulus, these sectors being preferably substantially equal to each other.

The corneal implant 1 subject of the present description preferably presents the outer peripheral ring 10 with a circular shape, whose diameter is between 1 mm and 20 mm, preferably between 5 and 10 mm.

The innermost peripheral ring 10, where present, preferably has a circular shape, whose diameter is between 0.1 and 10 mm, preferably between 0.5 and 7 mm.

The beams 21, 22, 40, the outer peripheral ring 10 and/or the innermost peripheral ring 11 can have a circular or polygonal cross-section, preferably polygonal with a number of sides of the polygon greater than or equal to three (for example, triangular, square, rectangular, pentagonal, etc.), more preferably rectangular.

The outer peripheral ring 10 and/or the innermost peripheral ring 11 having this circular or polygonal cross-section have a dimension of this cross-section in the plane of the peripheral rings 10, 11, or rather, a width, preferably in a range from 10 to 500 μm, more preferably greater than 30 μm and less than 300 μm.

The beams 21, 22, 40 preferably have a width in a range from 10 to 250 μm, more preferably greater than 40 μm and less than 150 μm.

Conversely, the outer peripheral ring 10, the innermost peripheral ring 11 and the beams 21, 22, 40 have a dimension of this cross-section in a direction perpendicular to the width or plane of the peripheral rings 10, 11, or rather a thickness, in a range from 5 to 250 μm, more preferably above 10 μm and less than 1000 μm.

If the cross-section of these rings and/or beams is circular, these two sizes will be substantially similar.

The reticular structure 20 can have coplanar beams 21, 22, 40 or on several superposed planes.

The beams 21, 22, 40 which intersect each other may have a thickness equal to the thickness of the reticular structure in the fields indicated above, or they may have a thickness equal to half the thickness of the reticular structure. In the latter case, the reticular structure 20 will show a thickness in the fields indicated above only in the areas of intersection of the beams.

The void portions 24 within the meshes of the reticular structure 20 preferably have a width between 100 and 2,000 μm, more preferably greater than 500 μm and less than 1,500 μm.

The corneal implant subject of the present description has mechanical and structural characteristics, in particular a rigidity superior to the rigidity of the corneal tissue, such as to impose its curvature on the cornea. This structural characteristic of the implant allows, following the surgical grafting of the implant within the thickness of the corneal stroma or under the corneal epithelium, to restore an optimal optical situation by converting corneas with deformations to regular shapes, for example, correcting compromising optical aberrations, such as, visual acuity or contrast sensitivity.

The rigidity of the human cornea, assessed by measuring Young's modulus, results in values from 0.01 to 10 MPa, preferably from 0.1 to 1 MPa.

In general, the rigidity of the corneal implant subject of the present description is preferably greater than 1 MPa, more preferably greater than 10 MPa, still more preferably included in a range from 10 MPa to 300 GPa.

The device also allows, due to its rigidity, reduction of optical aberrations generated both by the anterior corneal surface and by the posterior corneal surface in the case in which the implant is inserted inside the corneal stroma (where anterior and posterior are to be understood with reference to the corneal implant 1 insertion position inside the cornea), correction not obtainable with ablation by excimer or femtosecond laser or ring-shaped corneal implants or even implants made of non-rigid materials, such as tissue. In the event that the implant is positioned below the corneal epithelium, when the corneal epithelium regrows it will cover and incorporate the implant, assuming its shape.

Moreover, following surgical treatment that may envisage corneal dissection, the corneal tissue presenting a lower structural resistance than the pre-cut corneal tissue will better adapt to the new geometry imposed by the corneal implant with quantitatively higher optical results. In other words, the cornea within which the corneal implant has been inserted will have a structural rigidity suitable for the correct maintenance over time of the optical correction imposed by the corneal implant 1.

Moreover, in view of the rigidity of the corneal implant 1 described here, the implant is able to maintain its dome-shaped configuration also following stresses made during implantation (for example, due to manipulation of the implant by the surgeon) or daily use (for example, due to rubbing of the eye by the patient).

The device is indicated in all the pathologies that involve an irregularity of curvature of the cornea, preferably with useful stroma transparency, which cause optical aberrations that cannot be corrected, for example, with temple lenses or contact lenses, or in subjects that do not tolerate contact lenses.

Moreover, the device subject of the present description can be implanted in order to vary the corneal curvature in healthy subjects to correct a refractive error.

The main categories of patients targeted by the device include subjects suffering from non-inflammatory corneal ectasia (such as, for example, keratoconus and marginal pellucid degeneration or ectasia following corneal refractive surgical procedures) and subjects undergoing perforating keratoplasty or deep anterior lamellar with irregular or elevated astigmatism.

The use of the corneal implant 1 subject of the present description allows the following benefits to be obtained.

Thanks to the mechanical rigidity of the reticular structure, the corneal implant 1 allows the cornea to be modeled by imposing and obtaining a curvature defined a priori, contrary to what occurs with the use of ICRS (Intra corneal ring segments), and without tissue ablation, as happens in the case of ablative treatments with excimer or femtosecond laser, in which the final conformation of the cornea is not exactly predictable and the treatment is irreversible.

Moreover, thanks to the large area of void portions 24 of the meshes of the reticular structure with respect to the overall area of the reticular structure itself, the corneal implant subject of the present description i) does not interfere (or at most to a very negligible extent) with the passage of oxygen and other molecules through the corneal tissue anterior and posterior to the implant and ii) involves a reduction of the incoming light by 5-10% and of diffractive phenomena which are by far negligible when compared to the benefits gained by the implant 1 in terms of reduction of low-order (astigmatism) and high-order aberrations (such as coma and trefoil).

Thanks to the positioning of the corneal implant 1 near the nodal point of the eye, this implant is not substantially perceived by the patient.

The corneal implant 1 subject of the present description is implantable preferably in the corneal stroma or fixable to the anterior surface of the corneal stroma, below the corneal epithelium. The implant is also easily grafted and removable without (or with minimal) damage to the corneal tissue, greatly reducing pain in the postoperative period, speeding up visual recovery and thus improving the patient's quality of life.

The dimensions of the corneal implant 1, intended as the diameter of the outer peripheral ring 10, the diameter of the innermost peripheral ring 11 (if present), the radius of curvature of the dome-shaped structural body 2, as well as the thickness of the peripheral rings 10, 11 and/or of the beams 21, 22 and 40 are selected in such a way as to adapt to the specific needs of the patient and to the morphology of the cornea.

Corneal Implant Grafting Mode

The implant which is the subject of the present description can be grafted into the cornea of a patient by means of a conservative-additive refractive surgery that does not involve the removal of corneal tissue.

The device is preferably implantable in the corneal stroma, but can also be attached to the anterior surface of the corneal stroma, below the corneal epithelium or Bowman's membrane.

In the case of grafting within the corneal stroma, a circular pocket is formed in the stroma, preferably using a femtosecond laser with a quantifiable depth, in a range from 10 µm to 700 µm, preferably between 70 and 400 µm, with respect to the anterior corneal surface, or a flap of diameter quantifiable in a range from 3 mm to 11 mm, preferably between 5 and 9 mm and thickness from 50 µm to 500 µm, preferably between 70 and 400 µm, is prepared by microkeratome or femtosecond laser.

It is possible that the free edge of the flap or of the anterior layer to the pocket is attached to the adjacent tissue with stitches, or metal clips, or fibrin glue.

It is also possible to obtain a negative of exactly congruent shape to the corneal implant 1 in the corneal stroma by ablating tissue with excimer or femtosecond laser, into which the corneal implant is subsequently inserted.

Materials Usable for Making the Corneal Implant

The corneal implant 1 can be made using: metals and relative alloys (by way of example titanium (such as grade 1 or grade 2 titanium), nickel, cobalt, chromium, tantalum, gold, silver, iron and their alloys, such as steel, Nitinol, $Ti_6Al_4V$, AISI 301®, etc.), since the metals are preferably non-magnetic; carbon and its compounds, preferably inorganic; polymers; ceramic materials, and relative combinations.

The corneal implant 1 can also be made by using the aforesaid materials further mixed with other compounds such as hydroxyapatite, polylactic acid, polycaprolactone, fibroin, chitin, cellulose, chitosan, gelatin, carboxylmethyl cellulose, collagen (human or animal), hydrocolloid, hydrogel, Crabyon®, silver.

The corneal implant 1 can also be provided with an outer biocompatible and/or biodegradable coating optionally comprising a pharmacologically active principle, preferably anti-inflammatory, antibacterial and/or intended to inhibit or control the fibrotic reaction around the implant.

The outer coating can be made using compounds and/or compositions known in the field of implantable prostheses in an animal body for releasing active principles by implantable devices/prostheses. Particularly preferred materials for making a biocompatible and/or biodegradable coating of the corneal implant 1 are selected from: hydroxyapatite, polylactic acid, polycaprolactone, fibroin, chitin, cellulose, chitosan, gelatin, carboxylmethyl cellulose, collagen (human or animal), hydrocolloid, hydrogel, Crabyon®, silver and relative combinations.

Methods for Making the Corneal Implant

Below, some methods for producing a corneal implant as illustrated in FIG. 1 will be described, purely by way of non-limiting example.

A) Using a commercially pure Titanium sheet (CP, ASTM B 265, Grade 2 with a thickness of 0.05 mm Lamina S.p.A) as the starting material, the titanium sheet is subjected to a cutting operation by laser processing in order to produce the reticular structure 20 and the peripheral ring 10.

The laser processing is performed with the StarFemto FX laser with a source of ultrashort pulses (Rofin Baasel Lasertech GmbH & Co. KG) with the following process parameters:

Wavelength: 1030 nm
Focusing Optic: F100
Galvo Scanner Head: S14
Scan Speed of Galvo Scanner Head: 200 mm/s
Field Size: 40 mm×40 mm
Pulse duration: 250 fs
Pulse energy: 20 µJ
Repetition rate: 20 kHz Laser processing can also be carried out using a StarFiber 180FC fiber source (Rofin Baasel Lasertech GmbH & Co. KG). The result in terms of cutting precision is as good as the solution obtained with the StarFemto FX laser, but given the heat input, there is a deformation and a lower quality of the cut wall compared to that obtained with the StarFemto FX laser which mounts a source with ultrashort pulses.

Subsequently, a chemical electro-polishing treatment is carried out according to techniques widely known in the art in order to clean the surface and remove unwanted contaminants from the surface.

The pieces after electro-polishing can be subjected to a passivation/anodization treatment if the introduction of a color change of the piece is required.

The anodizing treatment of the individual titanium pieces is carried out according to the following procedure: the pieces are inserted into a basic aqueous solution of 10% ammonium sulfate, at room temperature for 10 s. The potential that is applied varies according to the desired color and, by way of non-exhaustive example, we report the following indications of the potentials to be applied and the colors obtainable:

Dark brown: 12-15 V;
Violet: 35-40 V;
Light blue: 25-30 V;
Blue: 30 V;
Yellow: 40 V.

In order to give the reticular structure a generally dome-shaped configuration, the piece is subjected to a drawing operation and subsequent coining with a mold formed by a die and a punch. Die and punch are made of tempered material (K100).

For producing corneal implant prototypes, the drawing and coining process is preferably carried out using a mechanical press with a precise mechanical laboratory toggle (GECHTER, SHKPU), punching precision of +/−10 µm, pressure value 9 Kg.

For small series productions, the drawing and coining process is preferably carried out using a press with electro-actuated descent of the puncher (ALFAMATIC, COLOMBO), punching precision of +/−10 µm, pressure value 9 Kg.

At the end of this step, a subsequent final cleaning (for example, in an ultrasonic bath) can be provided to remove any further residues still present on the surface of the corneal implant at the end of the production process.

The corneal implant can also be subjected to one or more mechanical, laser, chemical or other processes that have the purpose of modifying the surface morphology of the implant itself. Some possible processes are shot peening, corundum sandblasting and passivation treatment (which gives the maximum resistance to corrosion to the passive layer of oxide film, promoting its formation).

B) In the case in which the starting material is formed of an electro-welded net, this is subjected to a cutting operation by laser processing in order to isolate the reticular structure 20 and create the peripheral ring 10.

Subsequently, the production method can envisage carrying out all or only some of the steps already described previously with reference to the use of a starting material in the form of a sheet, such as electro-polishing, anodizing, drawing and any additional treatments intended to modify the implant surface morphology.

C) The corneal implant can also be produced by 3D printing of the final implant or in wax from which the implant subject of the present description is then obtained by lost-wax casting. In the latter case, the wax model is used according to the usual lost-wax casting techniques for producing the final component of the required material.

Determining Young's Modulus of the Corneal Implant

In order to determine Young's modulus of the device subject of the present invention, it is possible to perform tests of different types known to the expert, such as, for example, tensile tests 1) on the plate of the material with which the device is subsequently made, 2) on a single beam of which the device is constituted, or 3) on the final device.

In case 1), it is advisable to use an appropriately-sized tensile testing machine with respect to the tensile breaking loads of the material being tested; in this case the usable load cells can reach up to 2,000 kN.

In case 2), it is advisable to use an appropriately-sized tensile testing machine, equipped with load cells preferably in a range from 10 N to 10 kN, and it is necessary to have a representative beam obtained by the same technology as the device beam and of a length sufficient to perform the test, preferably greater than 20 mm.

In case 3) it is possible to use the same methods of case 1), while bearing in mind that the load applied in the first part of the tensile test will be used to flatten the dome-shaped device to make it planar, and will not be indicative for determining Young's modulus.

Of course, without prejudice to the principle of the invention, the structural details and the embodiments may vary widely with respect to what has been described and illustrated herein merely by way of example, without thereby departing from the object of the present invention as specified in the ensuing claims.

The invention claimed is:

1. A corneal implant designed for correcting irregularities of the corneal curvature of a subject, the implant having a dome-shaped structural body sized and configured to impose a regular curvature to corneal portions in contact with the implant,
   wherein the structural body comprises an outermost peripheral ring, an innermost peripheral ring, and an inner reticular structure in between the outermost and innermost peripheral rings, wherein the inner reticular structure comprises at least one first series of beams and at least one second series of beams intersecting each other and defining meshes having void portions, the beams of the first series having a respective first end connected to the outermost peripheral ring, the beams of the second series having a respective first end connected to the outermost peripheral ring, wherein the total area of the void portions within the meshes of the inner reticular structure is between 50% and 99.9% of the surface area of the inner reticular structure,
   wherein at least some the beams of the first series and of the second series have a respective second end connected to the innermost peripheral ring,
   wherein the innermost peripheral ring comprises a diameter ranging from 0.5 mm to 7.0 mm,
   wherein the corneal implant comprises a rigidity, assessed by measuring Young's modulus, ranging from 10 MPa to 300 GPa.

2. The corneal implant according to claim 1, wherein the outermost peripheral ring and the innermost peripheral ring are coaxial.

3. The corneal mplant according to claim 1, wherein the beams of the first series define—together with the outermost peripheral ring and the innermost peripheral ring—a plurality of sectors of the structural body, being substantially configured as an arc of a circular or elliptical annulus, said sectors being substantially equal to each other.

* * * * *